(12) United States Patent
Rosa

(10) Patent No.: US 9,084,629 B1
(45) Date of Patent: Jul. 21, 2015

(54) IMAGE GUIDED ATLAS CORRECTION

(71) Applicant: Scott L Rosa, Rock Hill, NY (US)

(72) Inventor: Scott L Rosa, Rock Hill, NY (US)

(*) Notice: Subject to any disclaimer, the term of this patent is extended or adjusted under 35 U.S.C. 154(b) by 0 days.

(21) Appl. No.: 14/044,804

(22) Filed: Oct. 2, 2013

Related U.S. Application Data

(60) Provisional application No. 61/709,104, filed on Oct. 2, 2012.

(51) Int. Cl.
 A61B 5/05 (2006.01)
 A61B 19/00 (2006.01)
 A61B 5/03 (2006.01)
 G01R 33/28 (2006.01)

(52) U.S. Cl.
 CPC ............. *A61B 19/5244* (2013.01); *A61B 5/032* (2013.01); *G01R 33/286* (2013.01)

(58) Field of Classification Search
 CPC ......... A61H 1/008; A61H 1/006; A61H 1/00; A61H 1/06; A61N 5/4566; A61B 2018/00339; A61B 5/4561
 USPC ...................... 600/411, 425; 378/63
 See application file for complete search history.

(56) References Cited

U.S. PATENT DOCUMENTS

2003/0195443 A1* 10/2003 Miller ........................... 601/108
2008/0312724 A1* 12/2008 Khan et al. .................... 607/115
2012/0184885 A1* 7/2012 Khan et al. ...................... 601/48
2013/0267876 A1* 10/2013 Leckenby et al. ............... 601/18

* cited by examiner

*Primary Examiner* — Long V Le
*Assistant Examiner* — Katherine McDonald
(74) *Attorney, Agent, or Firm* — Edward S. Sherman

(57) ABSTRACT

An external stylus provides an impulse to correct mal-alignments of the Atlas (C1). The placement and direction of the impulse is guided by the analysis of a plurality precisely placed or acquired tomographic images, preferably MRI images.

8 Claims, 18 Drawing Sheets

US 9,084,629 B1

IMAGE GUIDED ATLAS CORRECTION

CROSS REFERENCE TO RELATED APPLICATIONS

The present application claims the benefit of priority to the US Provisional Patent Application filed on Oct. 2, 2012, having application Ser. No. 61/709,104, which is incorporated herein by reference.

The application as filed contains one or more claims having an effective filing date after Mar. 16, 2013.

BACKGROUND OF INVENTION

The present invention relates to the treatment of spinal injuries, and more specifically to the use of functional MRI to guide chiropractic adjustment.

The present invention also relates to an improved method of spinal adjustment, and more specifically to the use of MRI or tomographic imaging methods that yield undistorted slice images to guide the adjustment of the atlas vertebrae.

SUMMARY OF INVENTION

In the present invention, the first object is achieved by a method of patient treatment comprising the steps of obtaining a first plurality of cine phase contrast MRI images to dynamically image a flow of at least one of cerebral spinal fluid (CSF) and blood, analyzing the cine phase contrast MRI to determine a potential correlation of misalignment or placement of at least one of C1-C7 with a coincident regions of abnormal flow of at least one of cerebral spinal fluid (CSF) and blood, externally adjusting C1 using a corrective impulse using at least one MRI image to determine the direction of the corrective impulse, obtaining a second plurality of cine phase contrast MRI images to dynamically image a flow of at least one of cerebral spinal fluid (CSF) and blood, determining if the step of external adjustment has corrected the abnormal flow of at least one of cerebral spinal fluid (CSF) and blood identified in the preceding step.

A second aspect of the invention is characterized by a method of patient treatment comprising the steps of obtaining a first plurality of cine MRI images to dynamically image the movement of the cervical spine of the patient as the head is moved from a least one of extension and flexion to neutral position while the patient is in an upright posture, analyzing the cine MRI to determine a potential correlation of misalignment or placement of at least one of C1-C7 and/or connective ligaments during the movement of at least one of extension and flexion, externally adjusting C1 using a corrective impulse using at least one MRI image to determine the direction of the corrective impulse, obtaining a second plurality of cine MRI images to dynamically image the movement of the cervical spine of the patient as the head is moved from a least one of extension and flexion to neutral position while the patient is in an upright posture, determining if the step of external adjustment has corrected the observed misalignment or placement of at least one of C1-C7 and/or connective ligaments observed in the first plurality of cine MRI images.

Another aspect of the invention is characterized by the method of patient treatment comprising the steps of obtaining at least one scout tomographic image of the skull and cervical spine, identifying a first one or more anatomic markers select from the alar ligament and the transverse ligament in the scout tomographic image, acquiring at least a second tomographic image in a plane orthogonal to the one scout tomographic image, wherein the second tomographic image extends through the at least one anatomical marker identified in the preceding step, identifying the position of a second plurality of anatomic markers in the at least second tomographic image, determining at least one vector component for orienting a stylus against at least a portion of the atlas from the positions of the second plurality of anatomic markers in the second tomographic image, energizing the stylus to provide a corrective impulse to the atlas in the direction of the at least one vector component, acquiring at least one third tomographic image to confirm the corrective placement of the atlas from said step of energizing the stylus.

Another aspect of the invention is characterized in any of the above methods of treatment wherein the vector component of the corrective impulse in the Y-axis coordinate is determined from an axial MRI tomographic image that includes at least one lateral mass of the Atlas and the Y-axis coordinate is the angle between; a horizontal reference line (HRL) that extends symmetrically from right to left sides of the skull, a second reference line that is perpendicular to a third reference line, wherein the third reference line to extends between the tip of a center of a bottom of a lateral mass of the Atlas to a center of a top lateral mass of the Atlas.

Another aspect of the invention is characterized in any of the above methods of treatment wherein the stylus approaches from above and forward of the sideways lying patient at the intersection of the mastoid bone and the ramus of the jaw to apply corrective force to the transverse process of the Atlas (C1).

The above and other objects, effects, features, and advantages of the present invention will become more apparent from the following description of the embodiments thereof taken in conjunction with the accompanying drawings.

DETAILED DESCRIPTION

Figure 1:
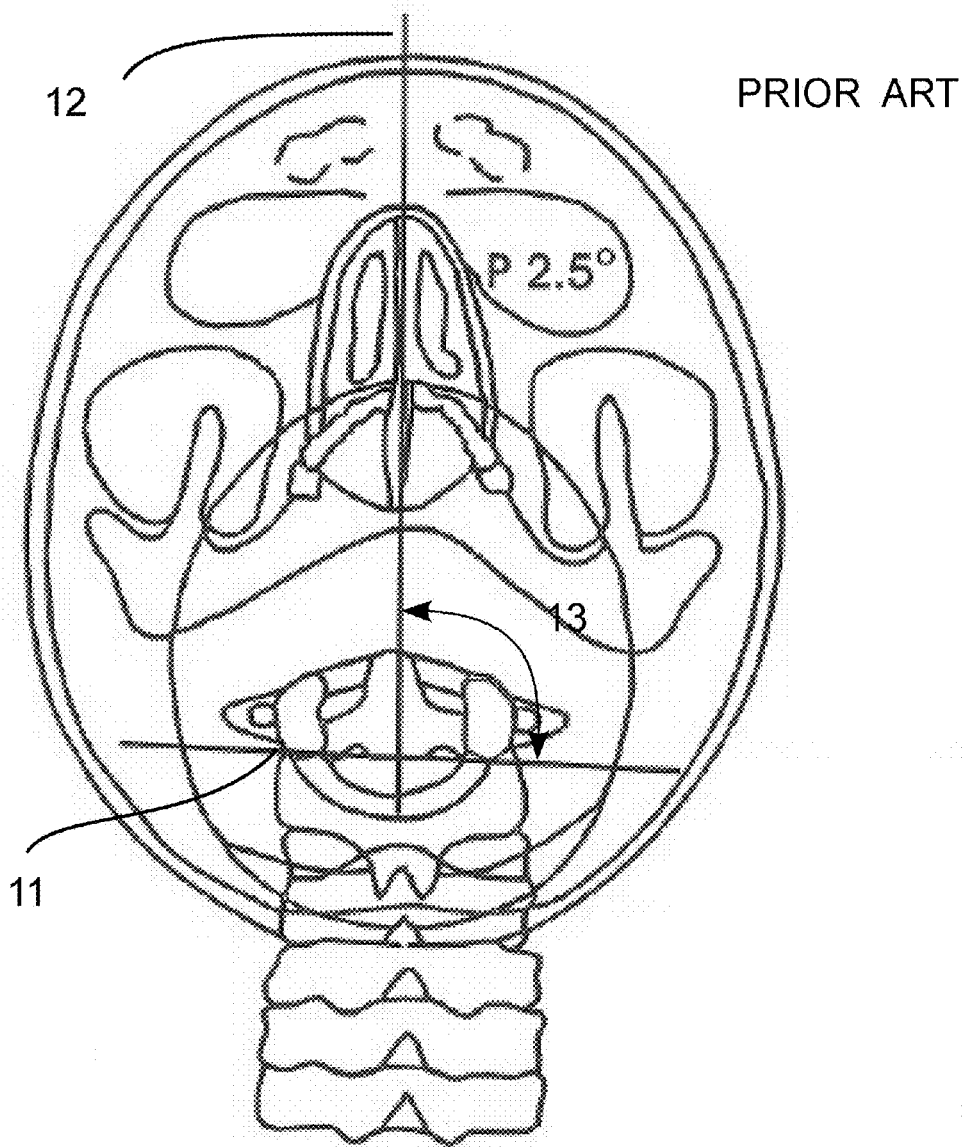
FIG. 1 is a schematic diagram of the use of an x-ray radiograph to calculate a correction vector component to restore the atlas (C1) to the normal position in a prior art method.

The Atlas Orthogonal technique is a method of spinal manipulation deployed by chiropractors in which the Atlas vertebra (C1) is restored to the correct position using a special instrument that applies a precise percussive impact to a portion of the atlas under a patient posture facilitates the return of the misaligned atlas with minimal resistance.

The instrument and its methods of conventional use are generally disclosed in Atlas Orthogonal Chiropractic Basic I and/or II, R.W. Sweat Foundation (1997), which is incorporated herein by reference. However, other instruments have been used to restore the position of vertebrae, and typically deploy a stylus that can be oriented to contact a portion of the patient believed to be effective in manipulating cervical or other spinal bones, either through a rapid mechanical displacement or percussive wave.

Chiropractic practitioners have traditionally used x-ray radiography to identify bone misalignments and plan corrective strategies, including both manual manipulation, passive correction with weights, or manipulation with instruments.

In the Atlas Orthogonal methodology as pioneered by R. Sweat, and described in the above manual, aspects of the misalignment of the Atlas are derived from an X-ray radiograph with the aid of templates to calculate the correction parameters. The correction parameter is the orientation of a corrective stylus, which is positioned on the patient by the practitioner according to a standard method. This parameter is essentially the direction in which the Atlas is urged back to the orthogonal position.

It has been discovered that alternative alignment methods are effective in restoring the Atlas (C1) and connected vertebra, including the Axis (C2) when anatomic measurements are made from properly oriented MRI images, and the corrective force is applied via a stylus in an alternative direction.

A stylus means a device having an intended point of contact with the body that can deliver a thrust or percussive wave in a predetermined direction to urge vertebrae into a desired position. This predetermined direction shall be referred to as a corrective vector.

It has also been discovered that the atlas correction can be more effective when MRI images of the atlas (C1), axis (C2) and the remaining cervical vertebrae (C3-C7) are used to make determine correction coordinates. This method is illustrated in FIG. 2 through 10, as discussed below with comparison to the convention method of FIG. 1. FIGS. 11-18 are process flow charts to illustrate the various and preferred embodiment of the imaging, analysis and treatment steps in the inventive method.

It should first be appreciated that the inventive methods are not limited to the preferred corrective stylus for the Atlas Orthogonal instrument, although it is preferred embodiment. Such a preferred stylus is at the tip 22 of a cylinder 21, with about a 1 to 5 mm diameter, that can provide a percussive impulse wave along the length of the cylindrical body without imparting significant bodily movement to the body, but the direction of the wave coincides with the axis of the cylindrical body 21. The cylindrical body 21 hence defines a corrective vector having predetermined Spherical or Cartesian coordinates derived from one or more body images. The body images used to determine the corrective vector are specific MRI images as disclosed herein, although it should be appreciated that X-ray tomographic sections, and possibly other forms of tomographic imaging could be used according to the other teaching in this application. However, as the MRI provides strong and pre-selectable contrast between different types of hard and soft tissue, it is preferred as providing a superior means to identify and deploy multiple significant anatomical markers in the images that are necessary to position various reference lines used to calculate the corrective vector. This is particularly important to additional embodiments of the invention in which image processing on a specialized or general purpose computer is used to identify the anatomic markers in "scout" MRI, which are used to plan the acquisition of additional MRI images in perpendicular reference planes, as well as to optionally construct reference lines and calculate the correction vector and/or patient positioning parameters.

The anatomic markers can also be derived from multiples MRI images of the same plane, in which the multiples images are acquired using different spin sequences to obtain contrast variations that are ideal for each anatomical marker. Alternatively, due to variation in the anatomy of some patients, which is sometimes due to deformities such as scoliosis, multiple adjacent image planes may be required to identify the anatomical markers that define the various reference lines used in the inventive method.

Magnetic resonance imaging (MRI) provides images of tissues not generally visible in x-rays, as well as bone. Rather than the images being a projection through the tissue and organ from the front to the back of the image plane, as in conventional x-rays images, like Computed Tomography (CT), MRI can be obtain of thin slices at different positions and orientations in any plane. Further, MR has much greater soft tissue contrast than X-ray CT making it especially useful in neurological, musculoskeletal, cardiovascular and oncological diseases. Unlike X-ray CT it uses no ionizing radiation. The scanner creates a powerful magnetic field which aligns the magnetization of hydrogen atoms in the body. Radio waves are used to alter the alignment of this magnetization. This causes the hydrogen atoms to emit a weak radio signal which is amplified by the scanner. This signal can be manipulated by additional magnetic fields to build up enough information to reconstruct an image of the body.

Recent improvement in MRI technology, as disclosed in the following U.S. Pat. Nos. 7,196,519; 6,677,753; and 6,828,792; which are incorporated herein by reference, have enabled commercial equipment for the acquisition of MRI in other than prone position, such as weight bearing position or any positions of a joint over a range of motion. Such equipment is currently available from Fonar Corporation 110 Marcus Drive, Melville, N.Y. 11747. It should be understood that the inventive method acquires the MRI images of the skull and cervical spine with the patient in an upright posture.

Further, the proper areas of the tissue must be imaged. Because MRI is so precise in its ability to image sections of tissue, care must be taken to select the appropriate series of sections as well as acquire the images under conditions in which the anatomical markers will stand out from adjacent tissue so that the diagnosis can be obtained, as well as evaluate tissue damage, improper joint mobility and constriction in arterial or venous blood flow, as well as the flow of Cerebral Spinal Fluid (CSF). That is the radiologist analyzing the MRI images must be able to look at the right location to see the thinning, tears, scar or other damage to the precise soft tissue to diagnose the injury and source of pain. This particularly problematic because such damage may be present in any of the three dimensions the damaged tissues occupies and at any orientation, thus it will be difficult to capture in a 2-dimensional image acquired by MRI.

MRI imaging parameters are MRI slice orientation (stack positioning), slice thickness (for optimal ligamentous, joint dysfunction assessment and accurate location of anatomical markers), spin sequence (to view soft tissue with sequences best used to reveal soft tissue pathology and provide sufficient contrast to identify anatomical markers) and where to acquire images that provide sufficiently precise locations of the required anatomical markers.

The MRI slice orientation and position is either axial (looking down the spine) or sagittal (looking at the spine in profile) as well as centered on a particular bone or junction. Anterior to posterior view (AP) or coronal views means facing the patient from the front so that the right and left sides are visible.

The MRI or other tomographic images are acquired in specific planes or slices to identify the important anatomic markers, as well abnormal pathology that might render different markers being deployed in the method. Generally, it is preferred that multiple parallel slices are obtained so the practitioner can select the most appropriate image for identifying the anatomical markers. Typically two or three "scout" views are recorded in the 3 orthogonal planes in Cartesian coordinates. These scout views then allow the accurate centering of the other views with respect to the spinal and cerebral anatomy of interest as discussed below.

Further, imaging parameters also includes a spin sequences, which refers to the precise nature of the magnetic field resonance and decay. These spin sequences are well known by the acronyms T1, T2, PD or PDI (proton density image), GRE, and phase contrast MRI, and the like and are well understood as commercial MRI equipment is available where the spin sequence is selected by the operator. Each such imaging parameter causes different types of cervical or joint tissues to appear lighter or darker in the MRI such that the anatomic markers disclosed herein are readily apparent, with the aid of anatomy reference guides and handbooks deployed by medical professionals. Cine imaging is the synthesis of a continuous image sequence form multiple frames, and can include a sequence that includes the patient's movement of the head from flexion to extension, as well as to visualize fluid flow that is initially revealed in phase contrast images. Such fluid flow includes Cerebral Spinal Fluid (CSF) as well as blood flow in arteries and veins. Such phase contrast images can also be analyzed to determine local fluid velocity, to quantify flow abnormalities.

A preferred application of cine MRI imaging is a method of patient treatment comprising the steps of obtaining a first plurality of cine MRI images to dynamically image the movement of the cervical spine of the patient as the head is moved from a least one of extension and flexion to neutral position while the patient is in an upright posture. The patient is instructed to move the head in stepwise increments while each separate image that forms the cine is recorded. Then, by analyzing the cine MRI it is possible to determine a potential correlation of misalignment or placement of at least one of C1-C7 and/or connective ligaments during the movement of at least one of extension and flexion. Accordingly, then applying the other teaching of the invention it is possible to externally adjusting C1 using a corrective impulse using at least one MRI image to determine the direction of the corrective impulse. Thereafter a comparable second plurality of cine MRI images can be obtained to dynamically image the movement of the cervical spine of the patient as the head is moved from a least one of extension and flexion to neutral position while the patient is in an upright posture. This enable as determination if the step of external adjustment has corrected the observed misalignment or placement of at least one of C1-C7 and/or connective ligaments observed in the first plurality of cine MRI images.

The T1 imaging mode reveals bone position and fracture, rim lesion, which is a tearing of a disk from attachment to vertebra body as well as distention of cranial elements through the foramen magnum (opening in skull where spinal cord descends). In contrast, T2 imaging mode reveal soft tissue, such as ligaments, spinal fluid, nerves, spinal cord, muscle tears, swelling and edema. FSE (fast spin echo) is a subset of the T1 and T2 modes. Proton density images (PD) or proton density weighted sequences imaging mode is specifically best suited to reveal ligaments in the cranio-cervical junction ie. (alar, transverse ligament, tectorial membrane, posterior atlanto-occipital membrane and the like). Slice orientation is very import to visualize the alar ligaments consistently. The gradient echo image (GRE) mode is preferred for acquiring axial (top down) disc images. According the cine MRI images of flexion and/or extension are preferably obtaining in PD mode.

Generally, speaking under such appropriate imaging mode/spin conditions normal ligament are typically dark, and expands along their length or breadth at constant and homogenous intensity and thickness. However, if the ligament is damaged, it may appear thin or disappear, if not show an actual tear.

The skilled radiologist, surgeon or chiropractor, when presented with the MRI images acquired under conditions described below will then utilize their intimate knowledge of normal tissue anatomy to recognize identify the required anatomic markers to practice the different embodiment of the invention. It should be appreciated that the invention is not limited to particular spin sequences, but may use any current or future MRI, including SD-MRI constructions, and X-ray or other imaging modality that may be subsequently discovered Alternatively, the software described below for image analysis may be operative to direct the computer to identify anatomic markers, direct MRI acquisition sequences, identify proper or best fit MRI image slices for identifying subsequent anatomic markers, derive reference line positions, and calculate the correction vector components therefrom.

Additional embodiment of the invention include the partial or full automation of the process sequences using image recognition software that is capable of performing may if not all of the steps described below.

Further, U.S. Pat. Nos. 5,974,165; 7,295,691; all of which are incorporated herein by references, provides further details on methods of detecting bony and other structures in grey scale images by computer means to provide a digital representation for further image processing and analysis. As is known in the art, the computer means may include a computer or computer-like object which contains a display, and a processing circuit (e.g., a microcontroller, microprocessor, custom ASIC, or the like) is coupled to a memory and a display. The display may include a display device, such as a touch screen monitor with a touch-screen interface. The computer or computer-like object may include a hard disk, or other fixed, high density media dives, connected using an appropriate device bus, such as a SCSI bus, an Enhanced IDE bus, a PCI bus, etc., a floppy drive, a tape or CD ROM drive with tape or CD media, or other removable media devices, such as magneto-optical media, etc., and a mother board. The motherboard includes, for example, a processor, a RAM, and a ROM, I/O ports which are used to couple to the image sensor, and optional specialized hardware for performing specialized hardware/software functions, such as sound processing, image processing, signal processing, neural network processing, etc., a microphone, and a speaker or speakers. Associated with the computer or computer-like object may be a keyboard for data entry, a pointing device such as a mouse, and a mouse pad or digitizing pad. Stored on anyone of the above described storage media (computer readable media), the system and method include programming for controlling both the hardware of the computer and for enabling the computer to interact with a human user. Such programming may include, but is not limited to, software for implementation of device drivers, operating systems, and user applications. Such computer readable media further includes programming or software instructions to direct the general purpose computer to performance in accordance with the system and method. The memory (e.g., including one or more of a hard disk, floppy disk, CDROM, EPROM, and the like) stores x-ray and/or MRI images.

Further, U.S. Pat. No. 5,099,859, which is incorporated herein by references, teaches means for x-ray image acquisition of joints and computer aided characterization of joint abnormalities. Further, other embodiment of the invention also contemplates alternate means of acquiring a digital representation of joints, and in particular the spine, such as is disclosed in U.S. Pat. No. 6,028,907, which is incorporated herein by reference.

In another aspect of the invention, the software is preferably operative to direct MRI acquisition of multiples images of different view with the appropriate slice orientation, spacing and spin parameters to allow automated detection of anatomical markers, which may include some of, but are not strictly limited to those disclosed herein. Further the software is also preferably operative to use the anatomical markers to mathematically construct appropriate reference lines for calculating the correction vector components used for atlas correction. The software is also more preferably operative to automatically identify the anatomic markers disclosed herein in scout views to center and position stacks of parallel images planes that are then subsequently acquired using the appropriate spin parameters, as well as the direct the operation of the MRI instrument to acquire additional images and identify the position of predetermined anatomical markers therein. The software is also preferably operative to transfer the correction vector components to the stylus 22 and cylinder supporting instrument, so that the stylus cylinder 21 axis can automatically oriented in the Y-Z planes for the corrective adjust of the patient's Atlas. However, it is highly preferable that each stage of the automation, calculations and stylus alignment can be reviewed by a clinician for approval, subject to manual refinement before each subsequent stage of image acquisition, analysis, calculation and corrective adjustment is performed. Accordingly, while it is not necessary for the generation of the reference lines in FIG. 3-8 for the mathematical calculation of the correction vectors, it is preferred that such lines and suitable highlighting of anatomic and derived or reference markers is generated and overlaid upon the MRI images to aid in the confirmation or adjustment of the same by the clinician. The operations would thus provide a valuable human supervisory and audit function before making an actual adjustment to the patient. Further, the supervisory and audit mode of operation described above can be performed remotely by a particularly highly skilled practitioner, for training or remote telemedicine delivery of medical services.

The Atlas adjustment is preferably conducted using an instrument that deploys a stylus 22 capable of delivering a percussive impulse while the patient is positioned in optimum posture and orientation for the corrective realignment of the Atlas. More preferably, the stylus 22 is supported in space on a platform that enables the orientation of the stylus relative to the along a vector that is optimum for the correction. Preferably the stylus percussive stylus is the type disclosed in U.S. Pat. No. 4,461,286 (issue to Sweat on Jul. 4, 1984), which is incorporate herein by reference. An instrument that supports the stylus on a platform relative to the patient and enables the precise orientation of the stylus for an optimum correction is disclosed in U.S. Pat. No. 8,152,747 (issued to Khan at all on Apr. 10, 2012), which is also incorporated herein by reference. U.S. Pat. No. 4,243,025A (issued on 1981 Jan. 6 to Jones), which is also incorporate by reference, also disclose an alternative adjusting device for directing a predetermined force against the cervical spine of the patient by means of a force-imparting stylus, the stylus being supported for universal adjustment with respect to the patient.

In order to better appreciate the advantageous distinctions of the inventive methods over the prior art, FIG. 1 is provided to illustrate the conventional method of determining one correction factor, the Y-axis components of the stylus percussive wave used to apply the corrective adjustment to the Atlas, xis, which is obtained from a plurality of the X-ray radiograph. In the conventional method, the atlas horizontal rotation is measured by observing an x-ray radiograph to observe the following atlas structures: 1. Lateral masses 2. Anterior roots, 3. Posterior roots, 4. Transverse processes 5. Posterior arch 6. Anterior arch. The practitioner then outlines the lateral masses, noting for example that: 1. They curve medially at their anterior (superior aspect of film) and posterior (inferior aspect of film) aspects. 2. The anterior lateral mass joins the anterior arch and should not project beyond it. 3. The posterior lateral mass ends close to the posterior root and should not project on or over the posterior arch. 4. The outer edge of the lateral mass will be at the edge of or slightly inside the transverse foramen. The foramina transversaria (transverse foramen) should be bilaterally situated lateral to and in the longitudinal middle of each lateral mass. If either the lateral masses or the foramina transversaria do not fit the above outlined criteria, it indicates that they are abnormally shaped.

If the lateral masses of the atlas are misshaped then the practitioner must decide which of the two structures are normal and then use that structure to determine the Atlas Horizontal Rotation. The conventionally preferred landmark for determining Atlas Horizontal Rotation is the lateral mass and more specifically, the posterior edge (inferior aspect on the film) of the superior facet of the lateral mass. If the lateral masses appear normal, then the practitioner is instructed to place the base of a protractor on the posterior (inferior aspect on the film) end of the lateral masses with its center aligned to the Horizontal Cephalic Line (HCL) and determine the extent that the Atlas has horizontally rotated in relation to the HCL. Note that this horizontal rotation will be assessed on the same side as the side of lateral rotation derived from the frontal radiograph. These conventional measurement is illustrated in FIG. 1., which illustrates the HCL (11) and the line (12) between the superior facets of the lateral masses of the atlas on opposing sides of the HCL, and the angle 13 between these lines which represents the atlas horizontal rotation angle.

It has been discovered that the X-ray radiographs used for calculating such Atlas rotations have additional limitation, as for example they may not distinguish Atlas abnormalities that are not visible, as well as distortion from being a projected image, as well as scatter of the x-ray beam by the more dense boney structures. Moreover, because of the image projection of an x-ray radiograph, certain views are not accessible, such as a pure or near pure axial view (head down), as this would require a full body exposure as well as produce an image in which the entire skeletal system contributions to x-ray attenuation, making the visualization of critical structures more difficult.

The inventor has realized that tomographic style slices, such as can be obtained by MRI or X-ray tomography, when acquired at the correct image planes, give superior views to identify and account for skeletal abnormalities, as well as plan a course of corrective treatment that appears to be surprisingly effective at both the rapidity of restoring normal anatomical structure, and relieving the adverse effects of misalignments. Moreover, patients appear to retain the corrections longer before needing additional treatments, as well as feel better.

Not wishing to be bound by theory, it is currently believed that the inventive method provides these surprisingly superior results because the Atlas and other vertebrae are restored to the normal position in a more natural manner that suffers from less resistance and potential trauma from contacting adjacent tissue, which must yield in some manner for the vertebrae to be relocated.

It has also been discovered that MRI images can be used to derive a more accurate corrective vectors for Atlas adjustment, that overcome the deficiencies of x-ray radiographs with respect to both observable and non observable bone deformities or malformations, as well as other limitations. Moreover, in addition to providing more therapeutically beneficial Atlas correction parameters, MRI images can also be used to better position the patient during the atlas correction procedure itself.

Again not wishing to be bound by theory, it has been observed that neuro-degenerative brain disorders such as multiple sclerosis, Parkinson's disease, dementia and ALS might be caused by aberrant CSF flow patterns into the brain/spinal cord. The use of cine and phase contrast software in upright patient positioned MRI instruments developed by Fonar Corporation has allowed the imaging of the cerebral spinal fluid flow to identify abnormalities in flow. To date, the abnormalities observed have all correlated in some manner with vertebra misalignment and/or soft tissue damage that narrow obstructs or interferes with the cerebral spinal fluid canal. Such MRI of the vertebral structure and the fluid flow allows the assessment and development of treatment methods to restore normal flow. The normal flow can be restored by inventive methods of characterization, calculation, and corrective manipulation disclosed herein.

Figure 2A:
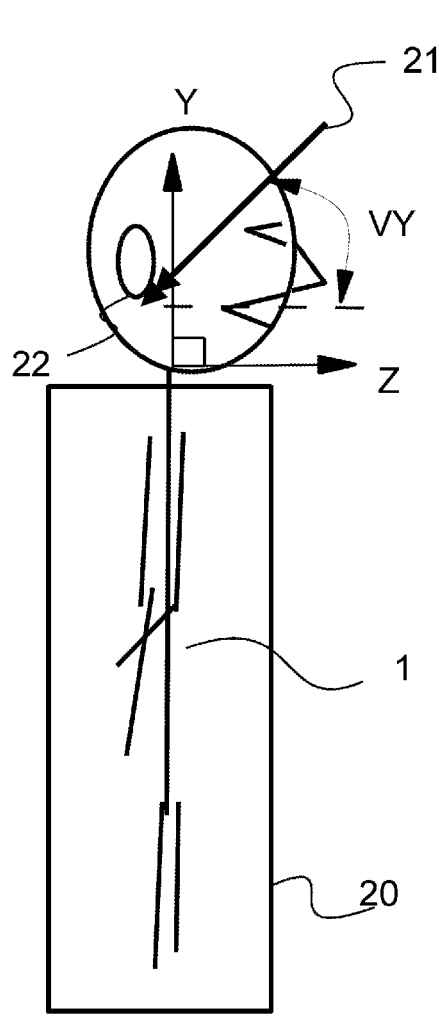
FIGS. 2A and 2B are schematic diagram of patient and corrective instrument positions in the inventive treatment method in which the patient is shown in plan view in FIG. 2A and front elevation view in FIG. 2B.
Figure 2B:
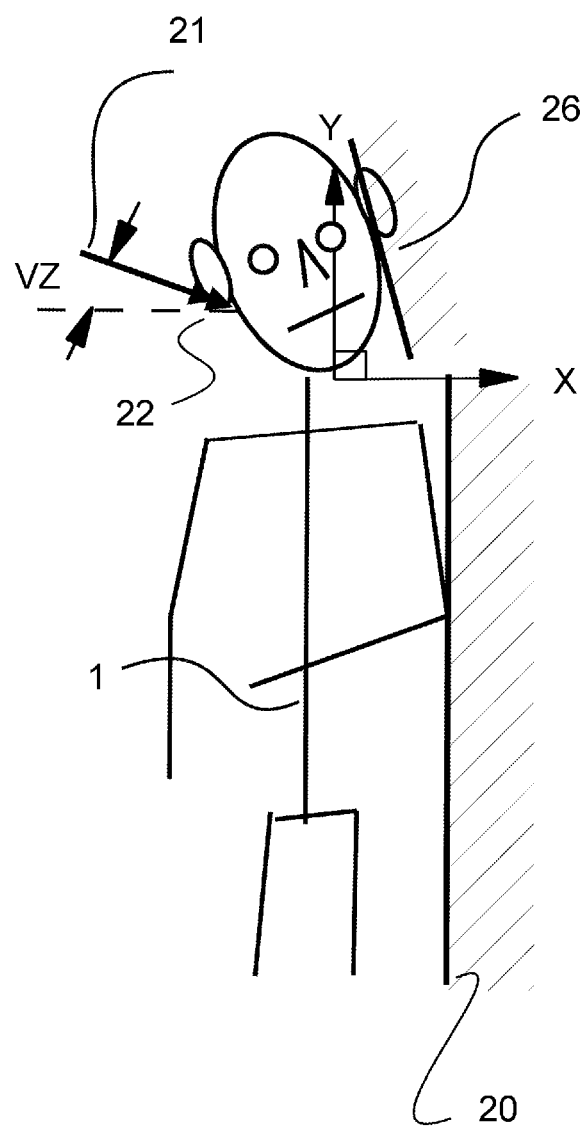

Referring now to the inventive method in FIGS. 2A and 2B, the stylus 22 direction during the application of a percussive wave is a vector that coincides with the cylinder 21 axis. The preferred vector has a Y and Z component that are calculated from multiple MRI images. The Y and Z components are shown in FIGS. 2A and 2B with respect to the patient's 1 position on a treatment platform or table 20, along with the preferred method of placement of the patient 1 head on the head support 26, as well as to illustrate the point of contact of the body with the stylus 22. It is currently preferred that the stylus 22 approaches from above and forward of the sideways lying patient 1 at the intersection of the mastoid bone and the ramus of the jaw, where it will apply corrective force to the transverse process of the Atlas (C1). The z-axis component of the correction vector corrects lateral misalignment of the Atlas (C1), whereas the Y-axis components of the correction vector corrects rotational misalignment of the Atlas (C1). The treatment of the patient comprises the process step 940-943 to position the patient, set up the stylus 22 and cylinder 21 at the Z and Y coordinates, and 950 to treat the patient, as well as 951 to energize the stylus 951 and step 952 to use at least some of the same MRI images to verify correction of the Atlas to a proper orthogonal position.

As the Z-axis correction calculation is more complex it will be described first with respect to FIG. 3-8. The Z-axis correction calculations are very similar to the traditional Atlas Orthogonal method, but differ primarily by the use of multiple MRI images, or comparable anatomic slices that might be obtained by x-ray tomography, where MRI not available.

Figure 4:
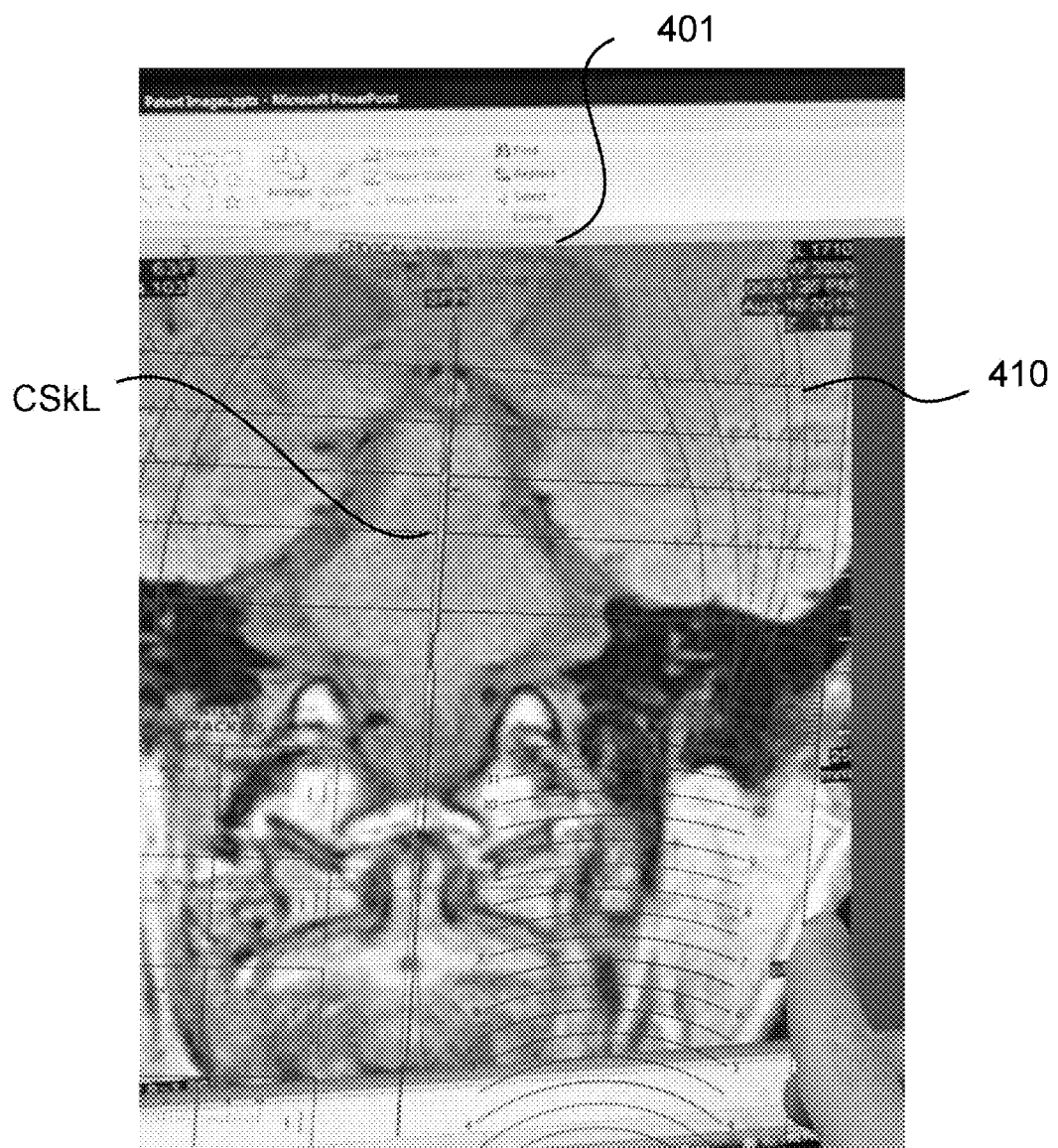
FIG. 4 is an MRI image of the ORL plane identified in FIG. 3, showing the use of a template to draw the Center Skull Line (CSkL).
Figure 5:
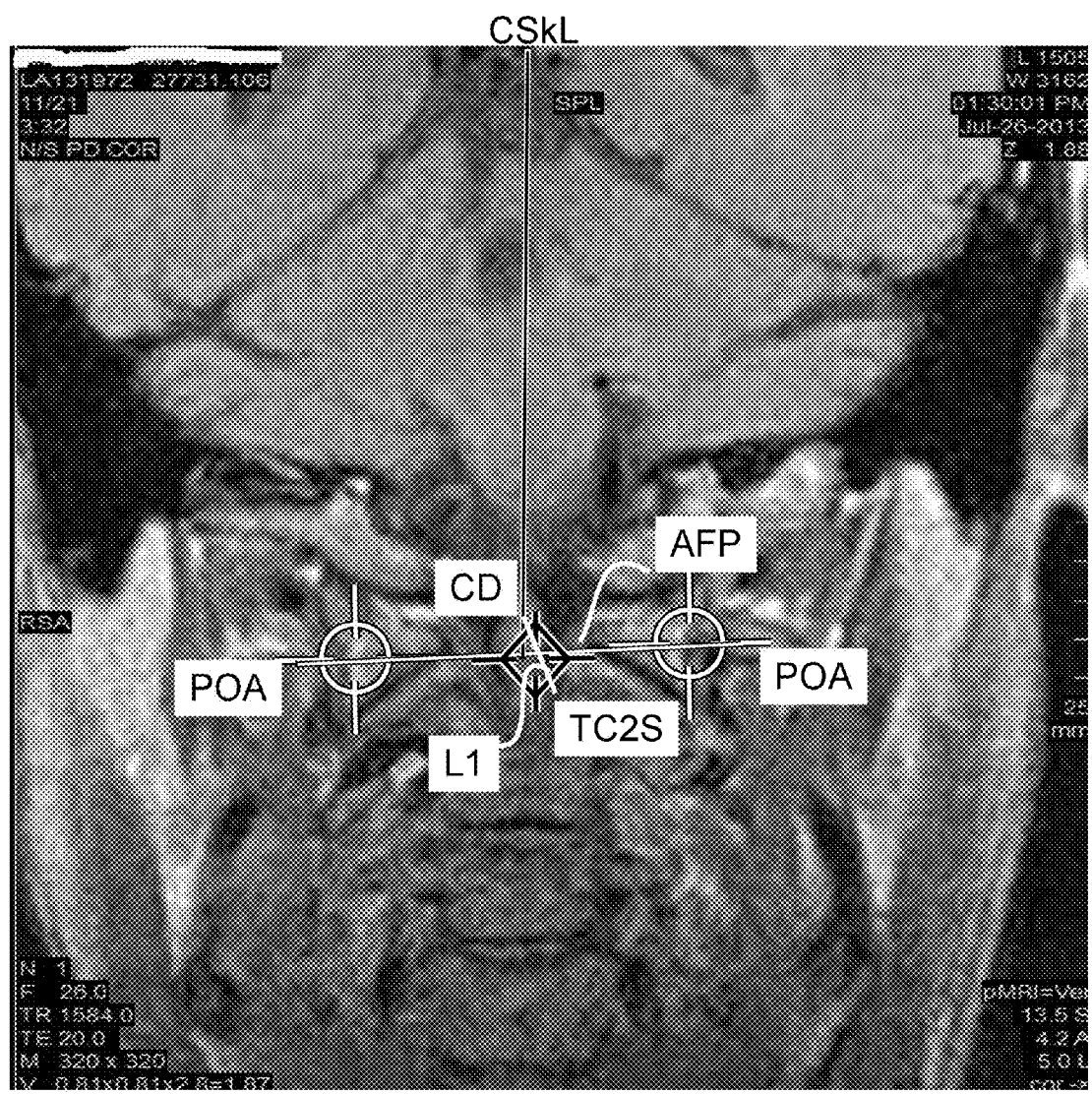
FIG. 5 is an MRI image of the ORL plane identified in FIG. 3, showing the anatomical markers that define the Atlas Frontal Plane Line (AFP) that is used to determine a component of the correction vector Z-axis components in the inventive method.
Figure 6:
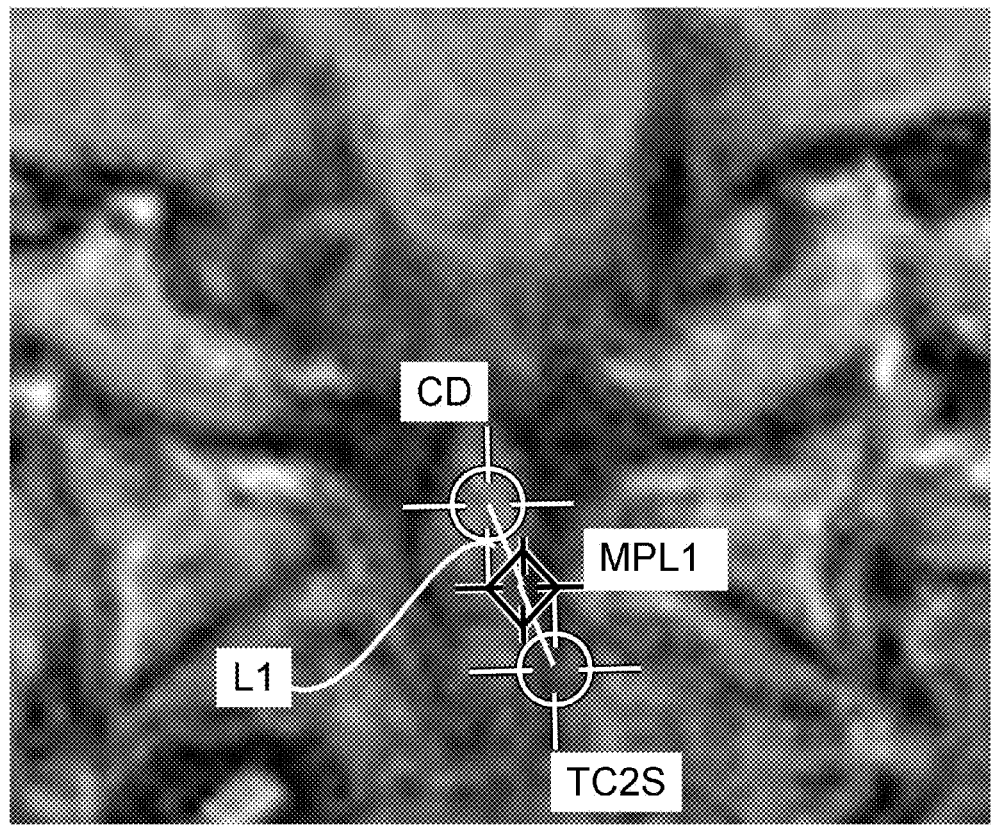
FIG. 6 is an enlarged portion of the image of FIGS. 4 and 5 showing additional anatomical markers that define a reference line that is used to determine a component of the correction vector Z-axis components in the inventive method.
Figure 12:
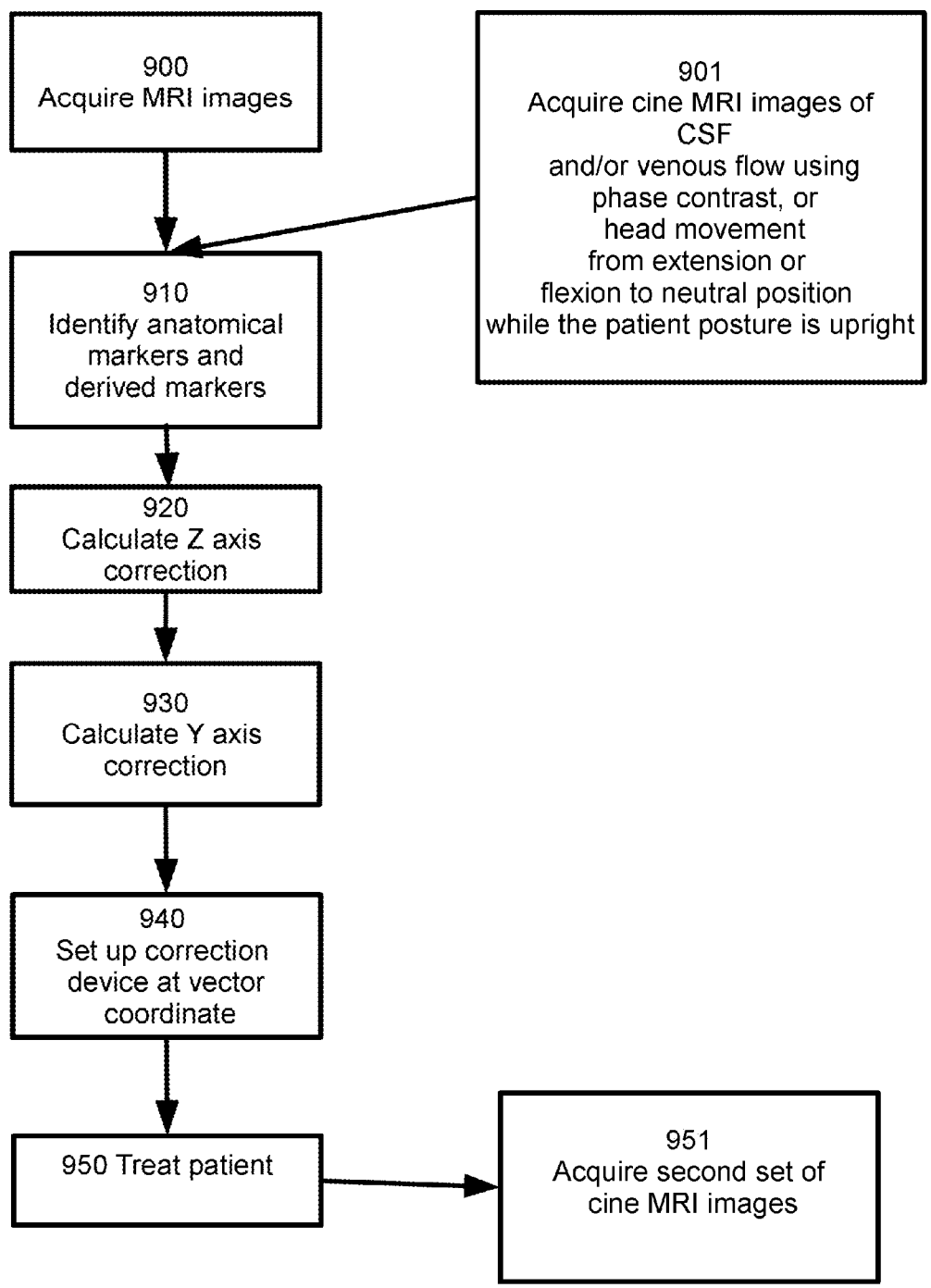
FIG. 12 is another process flow chart providing an overview of another embodiment of the imaging, analysis and treatment processes.
Figure 13:
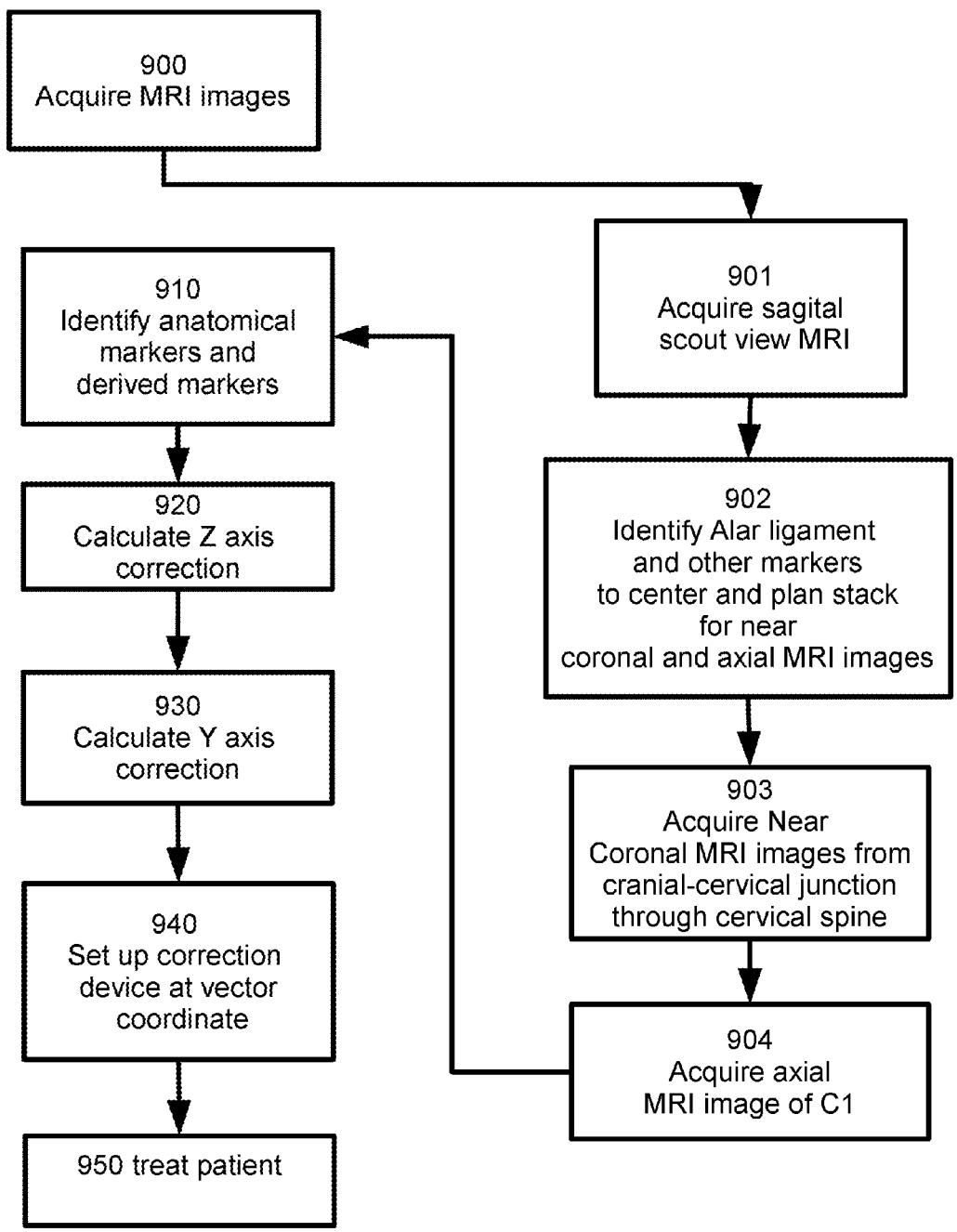
FIG. 13 is a process flow chart corresponding to FIGS. 11 and 12, but showing sub process steps used in acquiring multiple MRI images.
Figure 14:
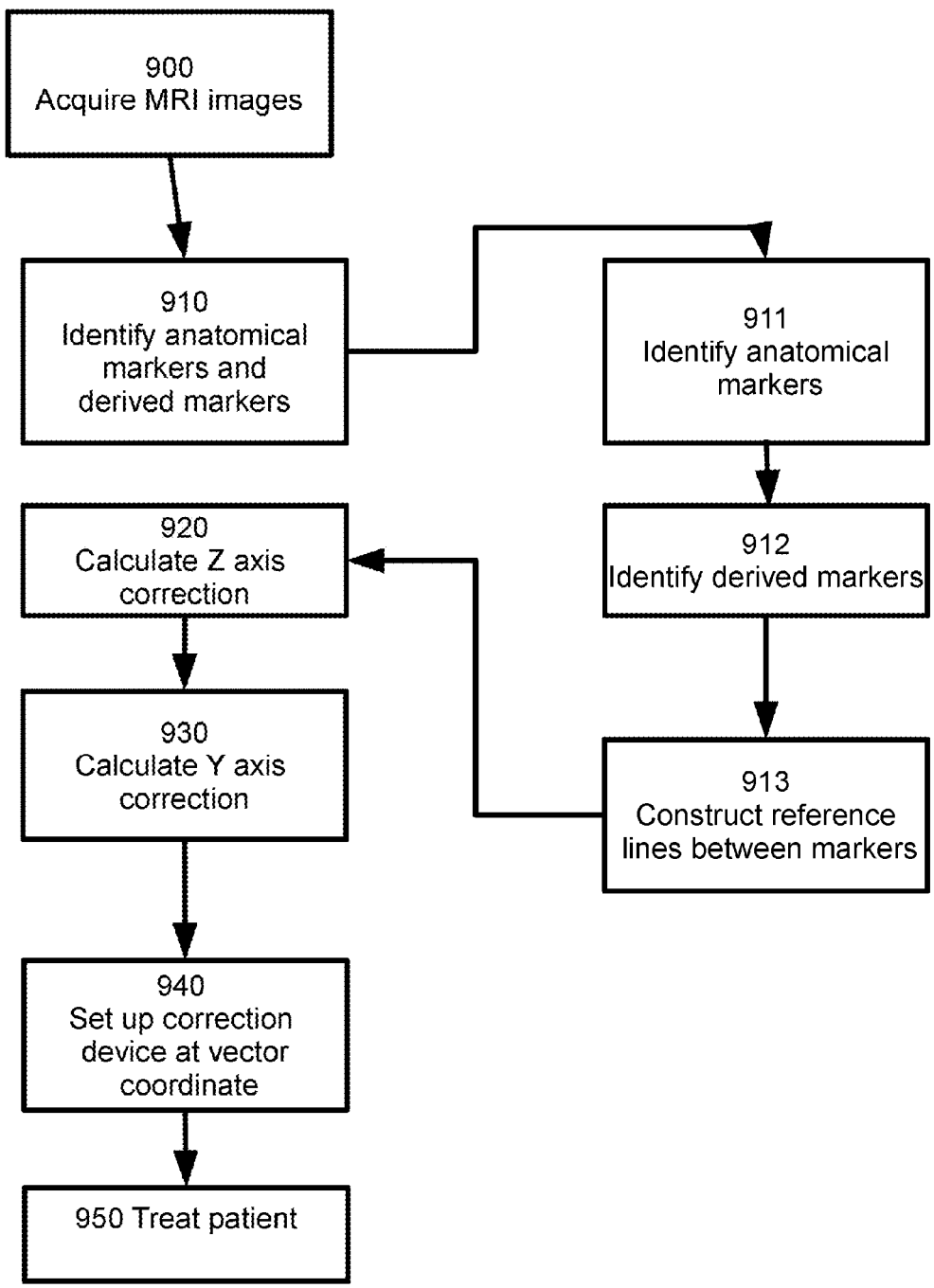
FIG. 14 is a process flow chart corresponding to FIGS. 11 and 12, but showing sub process steps used in identifying the anatomical markers and reference lines used to calculate the corrective vector of the stylus applied in the step illustrated in FIG. 2.
Figure 15:
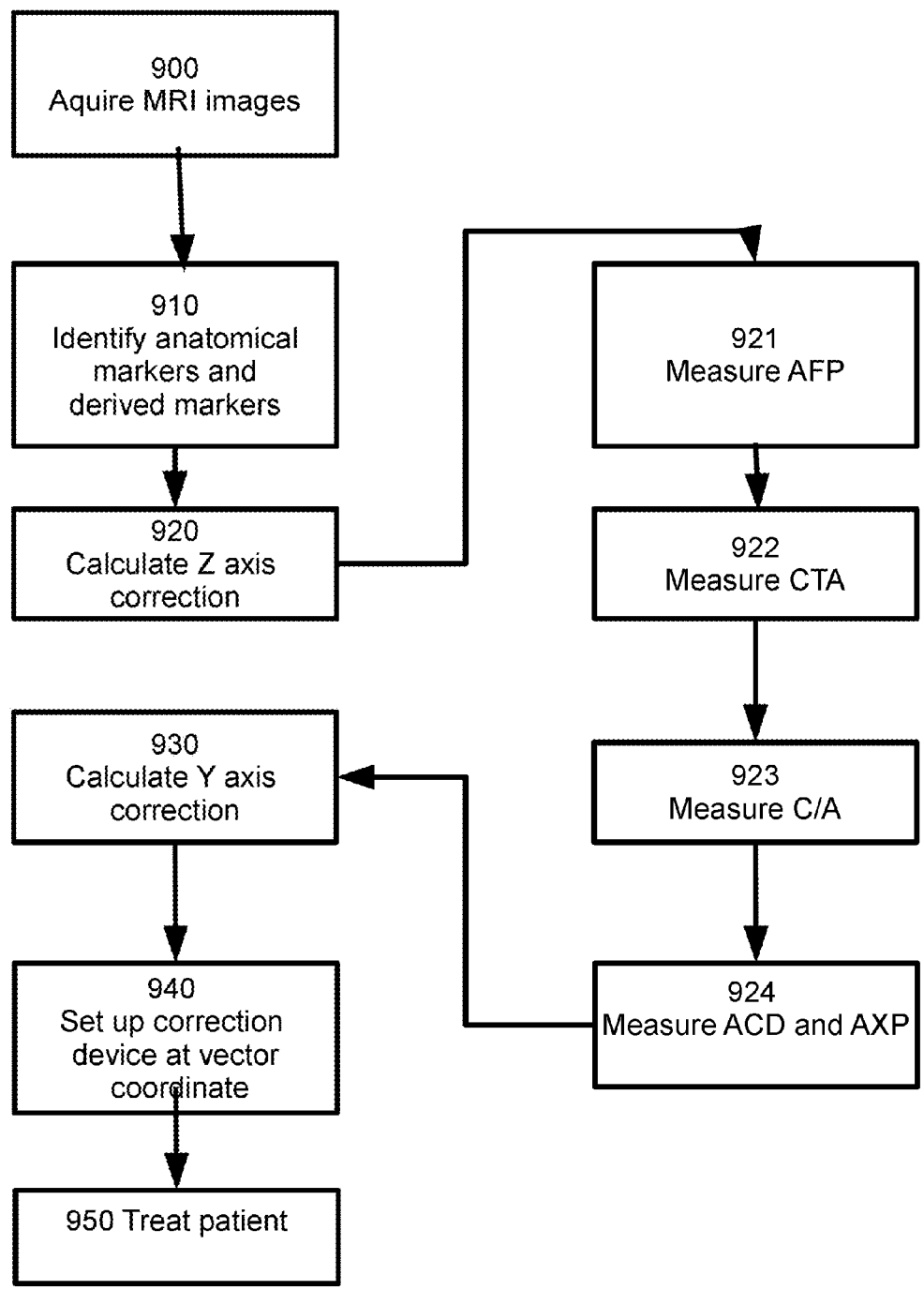
FIG. 15 is a process flow chart corresponding to FIGS. 11 and 12, but showing sub process steps used in calculating the Z-axis component of the correction vector.
Figure 16:
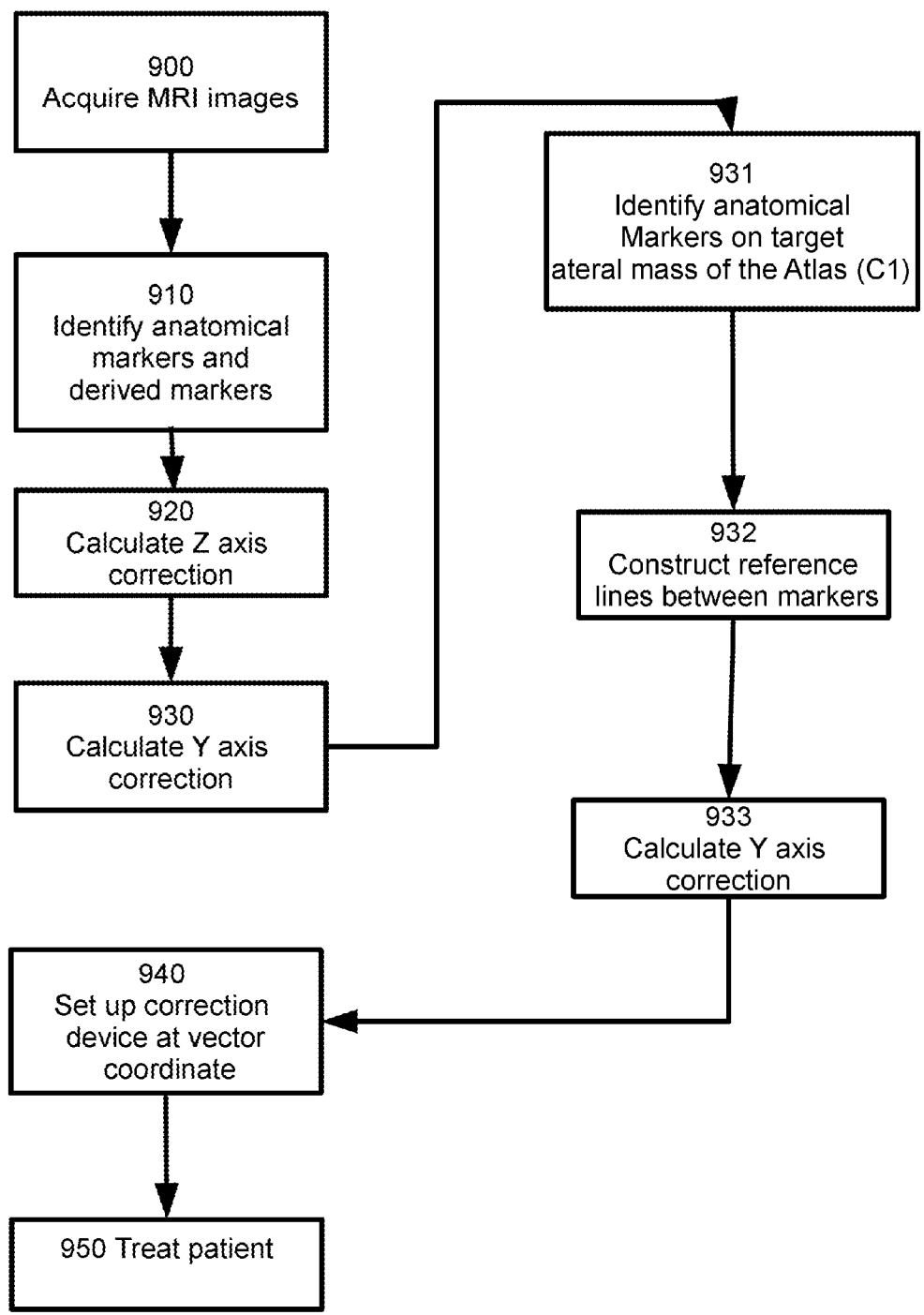
FIG. 16 is a process flow chart corresponding to FIGS. 11 and 12, but showing sub process steps used in calculating the Y-axis component of the correction vector.
Figure 17:
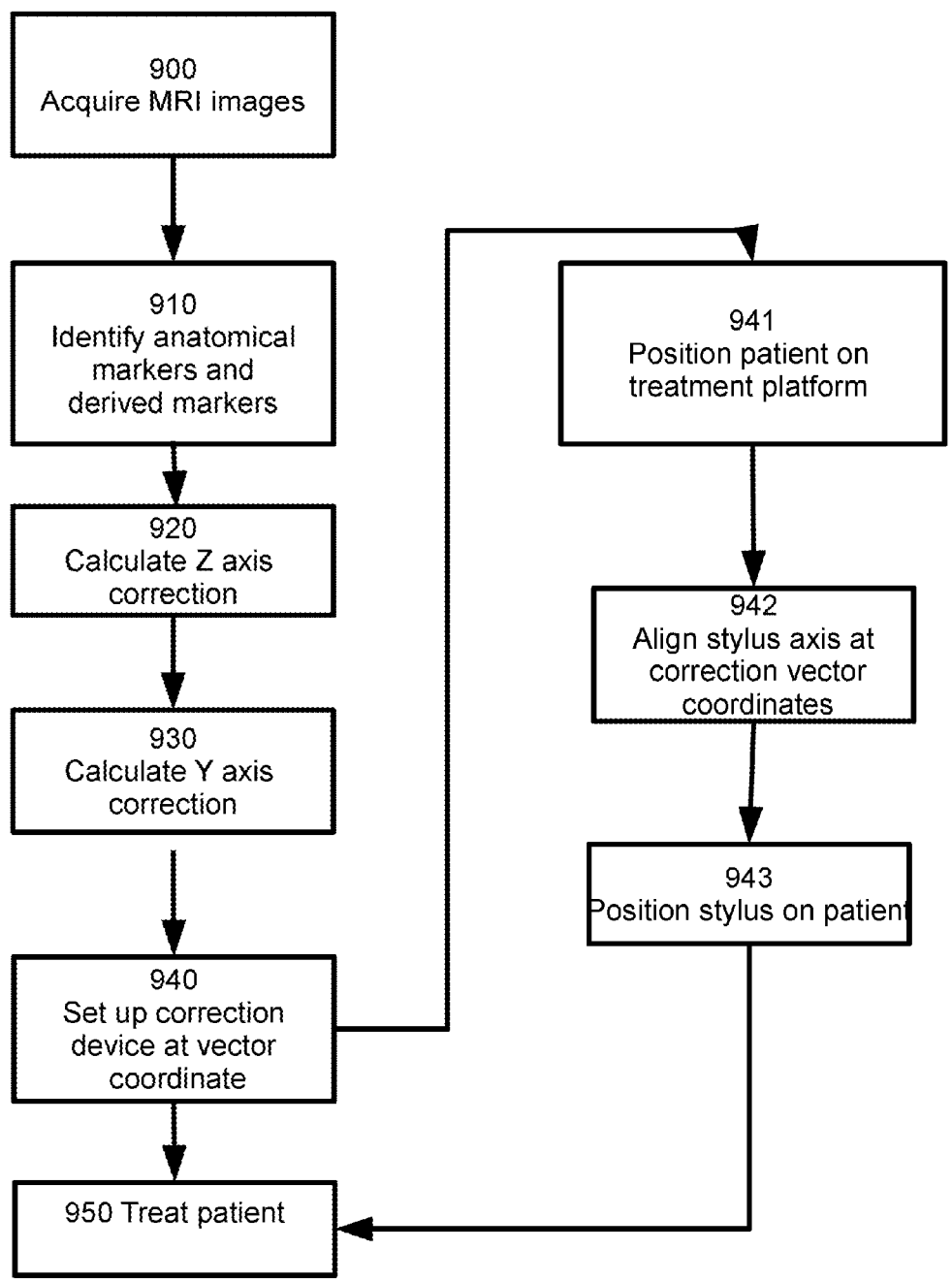
FIG. 17 is a process flow chart corresponding to FIGS. 11 and 12, but showing sub process steps used to set up the instrument shown and descried with respect to FIG. 2 to treat the patient.
Figure 18:
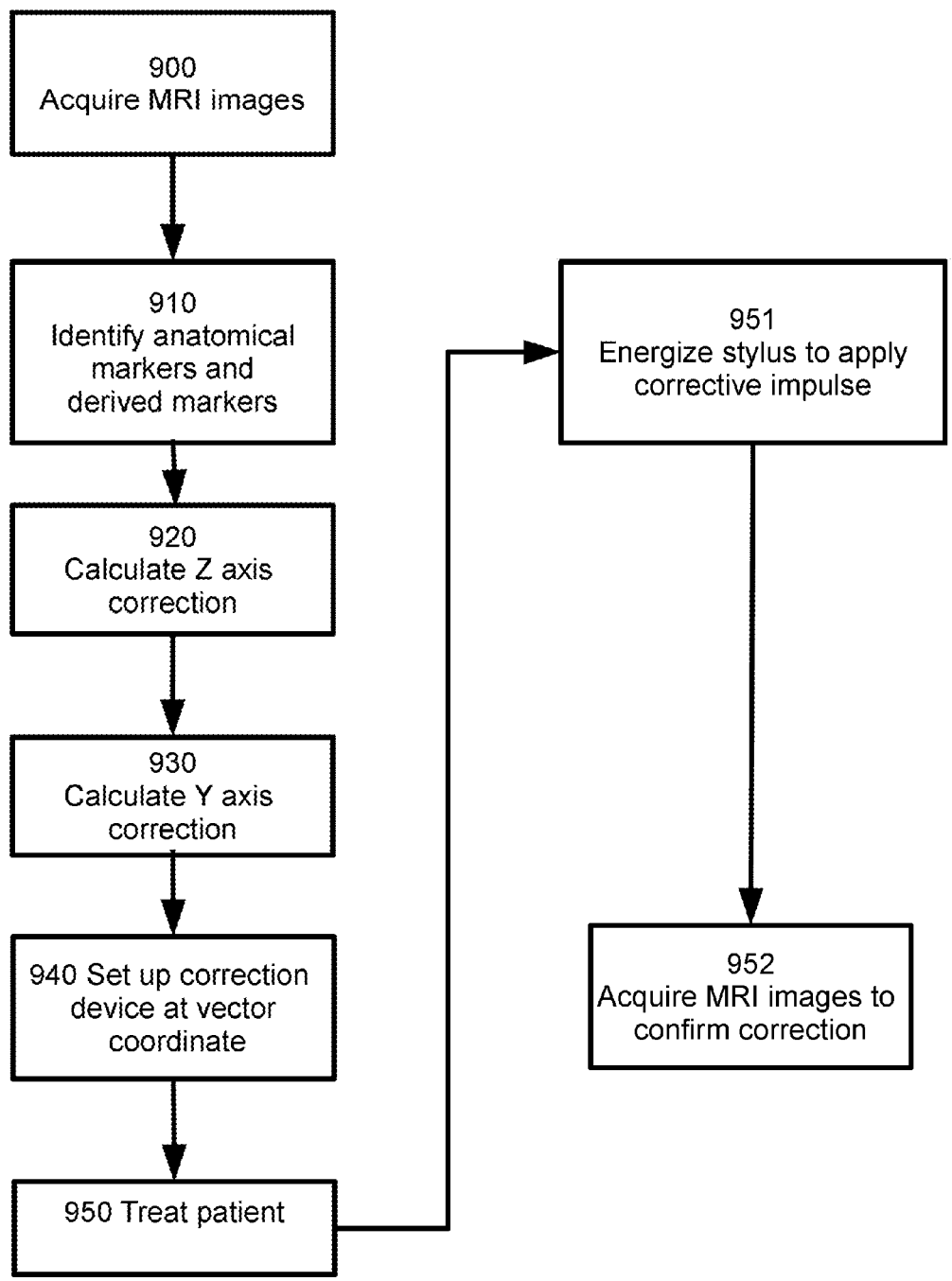
FIG. 18 is a process flow chart corresponding to FIGS. 11 and 12, but showing sub process steps used to treat the patient.

Accordingly, the anatomic markers used to derive the Z component of the corrective vector in a preferred MRI image slice are illustrated in FIG. 4-6, and correspond to process steps 910 to 913 in FIG. 12.

In contrast, the Y-axis component correction calculation is relatively simple, but results in a very different Y-axis vector component than the traditional Atlas Orthogonal method, labeled as prior art in FIG. 1. The novel resulting Y-axis component placement of the stylus 21 has proved effective in collaboration with the preferred stylus placement described with respect to FIG. 2. Normally, the Z-axis analysis is performed first, as it yields a direction for performing the Y-axis analysis.

Accordingly, in the first step of the process of determining the Z-axis correction, shown in the flow chart in FIG. 900-903, a sagittal MRI "scout" image of the head and upper cervical region is obtained preferably using a proton density (PD) spin sequence, during image acquisition (step 901). This MRI image is illustrated in FIG. 3, and also illustrate the placement of a series of parallel spaced apart image planes used to obtain addition PD images (step 903), from which the Z-axis component of the correction vector is calculated.

Figure 3:
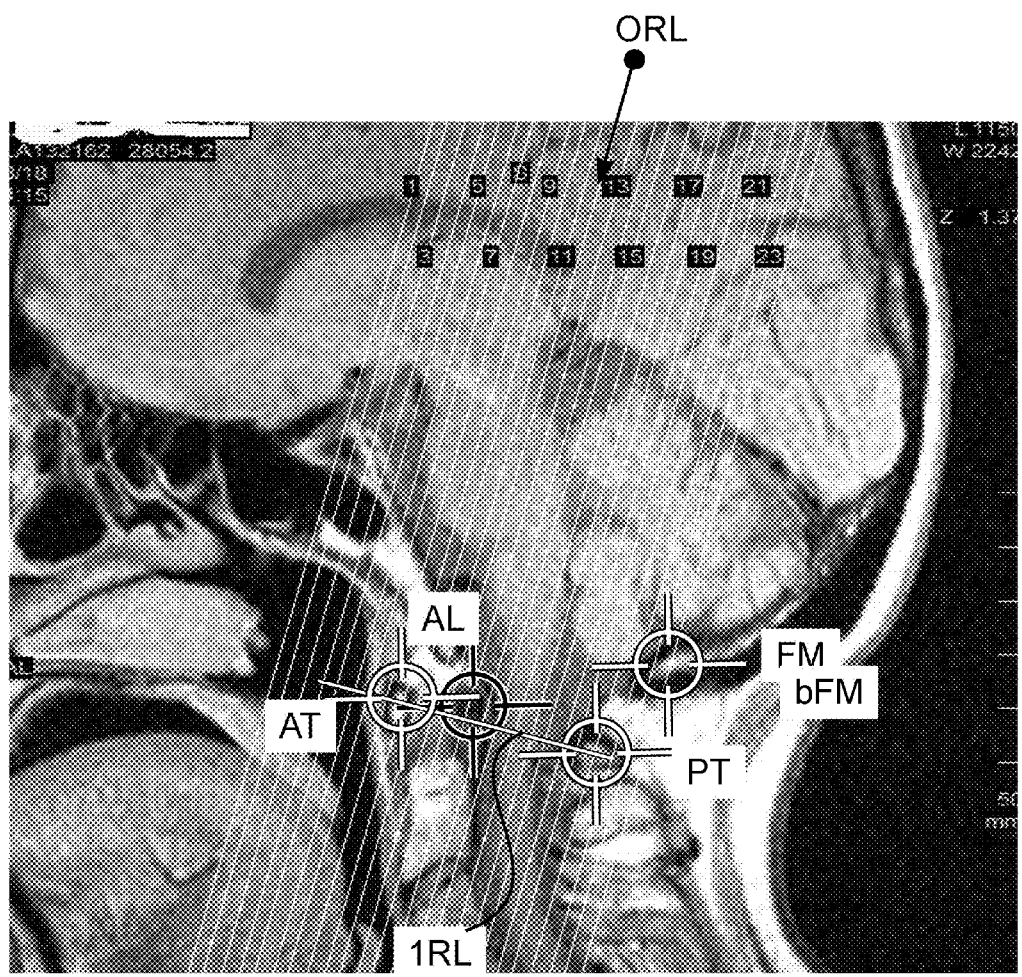
FIG. 3 is sagittal MRI "scout" image (PD spin sequence) of the patient's skull and upper cervical region used to position a series of parallel images planes for subsequent MRI acquisition, which are then used to identify anatomical reference points deployed in subsequent calculations of vector components of the stylus deployed in the treatment illustrated in FIGS. 2A and 2B.

Thus, FIG. 3 is sagittal MRI image used to position a series of parallel images planes for additional MRI images. One or more of these additional MRI images are used to identify anatomical reference points used to determine correction vector components in the inventive method. This sagittal view was acquired with a PD spin sequence. In order to set the placement of the subsequent views, which are acquired at parallel spaced apart substantially orthogonal planes noted on the image a "stack" or sequence of parallel spaced apart planes is centered at the Alar Ligament (AL). The orientation of the parallel lines is approximately 5 to 15 clockwise from the orthogonal reference line (ORL) to the 1$^{st}$ reference line (1RL). 1RL extends from the anterior tubericle (AT) to the posterior tubericle (PT) of Atlas (C1). Clockwise in this view, with the eyes looking to the left, means from in front of chest upward to a position behind the head. If the patient is oriented to look toward the left, then the orientation of the parallel lines would be from about 5 to 15 degrees counter clockwise.

It should be noted that to obtain other clinically useful information, it is preferable that the stack extends from 6 to 9 mm forward of the AT to past the back of the foramen magnum (bFM) of the by 6-9 mm. The foramen magnum (FM) is labeled FM. The lines in the stack are preferably spaced apart by not more than 3 mm, but more preferably by about 2.8 mm or less.

The MRI images (FIG. 4-8) corresponding to one more images in the stack in FIG. 3 may be considered near coronal in orientation, as the process of selecting this orientation with respect to anatomical markers that define line 1RL is set the orientation within 5 to 15 degrees from a vertical orientation. Centering the stack on the AL with reference to ORL provides that other anatomical markers used to calculate the Z-axis component of the correction vector will be visible free of the distortion that is inherent in the x-ray radiographs used in prior art methods.

Hence, FIG. 4-8 are such near coronal MRI image of a plane identified in FIG. 3 as ORL used to identify anatomical markers in process steps 910-913, which are used to determine the Z-axis component of the correction vector in process steps 920-924.

The Z axis calculation involves the identification of multiple anatomical features, which are connected by different sets of references lines, from which three different angular parameters, know as work factors are measured. These three work factors are the Atlas Frontal Plane displacement of work factor (AFPwf), Circular Tangent Angle (CTA) and Atlas Displacement over Cervical Plane (A/C). The numeric sum of the AFPwf, CTA and CA angles are the Z axis component of the correction vector (VZ) is shown in FIG. 2B extending between the stylus cylinder 21 and the Z-axis.

The lines used to measure the work factor parameter angles are drawn from specific anatomical markers on the appropriate MRI image plane. In this application, the anatomic markers are denoted by enclosure within round "gunsight" style markers and are labeled with the abbreviated names, whereas reference lines that are subsequently used to measure angles extend from the mid point of these anatomical markers, and are also labeled with the abbreviated names.

Reference lines are also drawn between derived markers, which are determined as disclosed below from the anatomic markers. These derived markers denoted by enclosure within diamond shaped "gunsight" style markers, and labeled with abbreviated names. Some reference lines are drawn between these derived markers.

FIG. 4 is photograph of showing the use of a transparent template 401 taught in the Atlas Orthogonal Chiropractic Basic I and II manual being superimposed over the near coronal MRI image at ORL line. The template 401 is displaced and located so pick the pairs of arched lines 410 on the template are the best fit the external skull outline. The Center Skull Line (CSkL) is then drawn down a slot in the middle of the template.

FIG. 5 is the near coronal MRI image (PD) at the ORL line illustrating how the Central skull line (CSkL) extends vertically through the center of the skull, and ends just above the Dens of the Axis (C2). FIG. 5 also illustrates the Atlas Frontal Plane Line (AFP) that extends from and connects the point of attachment (POA) of the posterior arches of the lateral masses of Atlas (C1)

FIG. 6 is an enlarged portion of FIG. 5 that shows anatomical markers and a derived marker that define the upper end point of the Cervical Spline Line (CSpL) in FIG. 6. The CSpL descends downward (in FIG. 7) from a derived marker at the mid point (MPL1) of the line L1. L1 extends from the center of the dens of C2 (CD) to the tip of the C2 spinous (TC2S).

Figure 7:
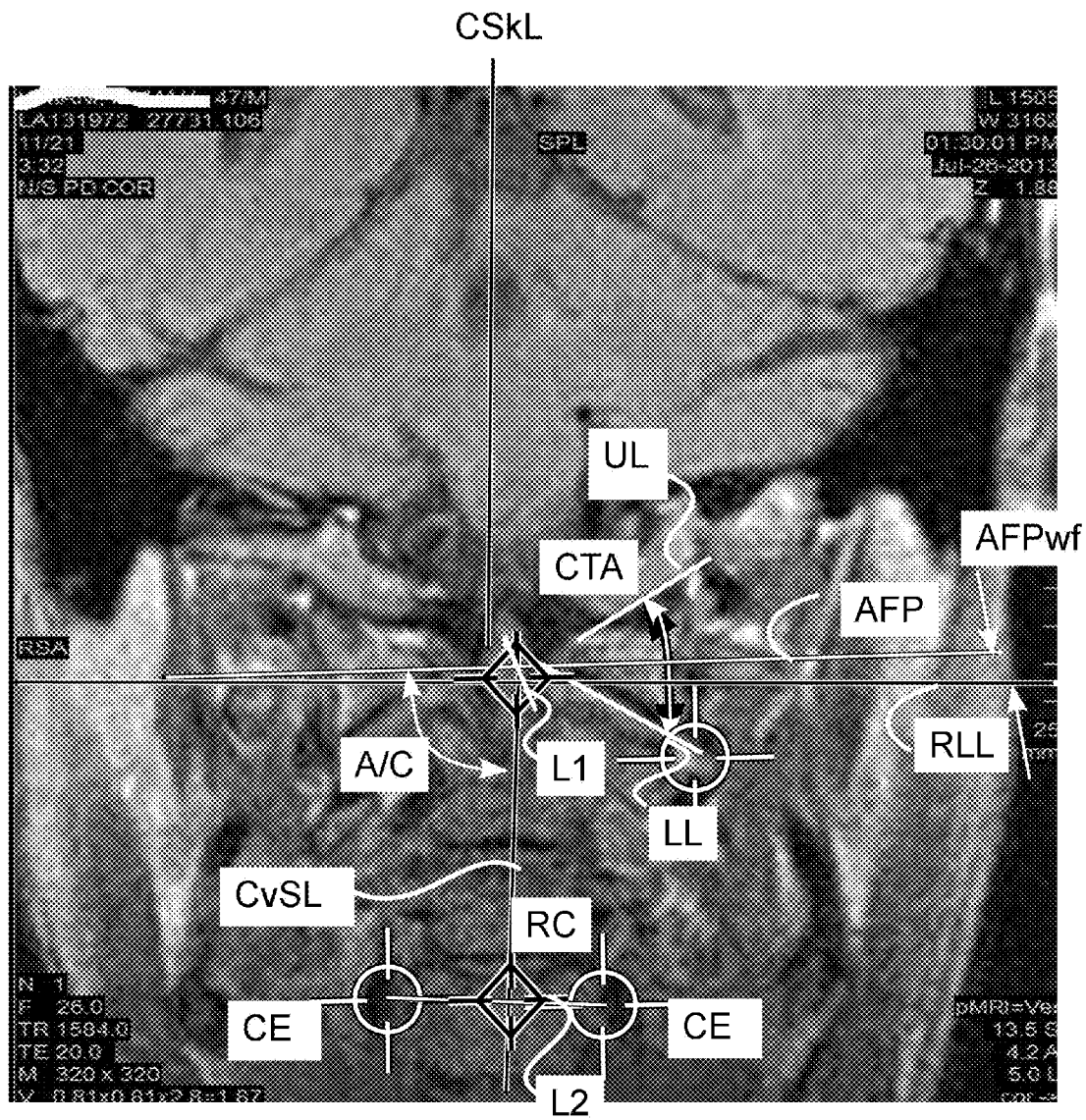
FIG. 7 is the MRI image of FIG. 4 showing additional anatomical markers that define additional reference lines that are used to determine a component of the correction vector Z-axis components in the inventive method
Figure 8:
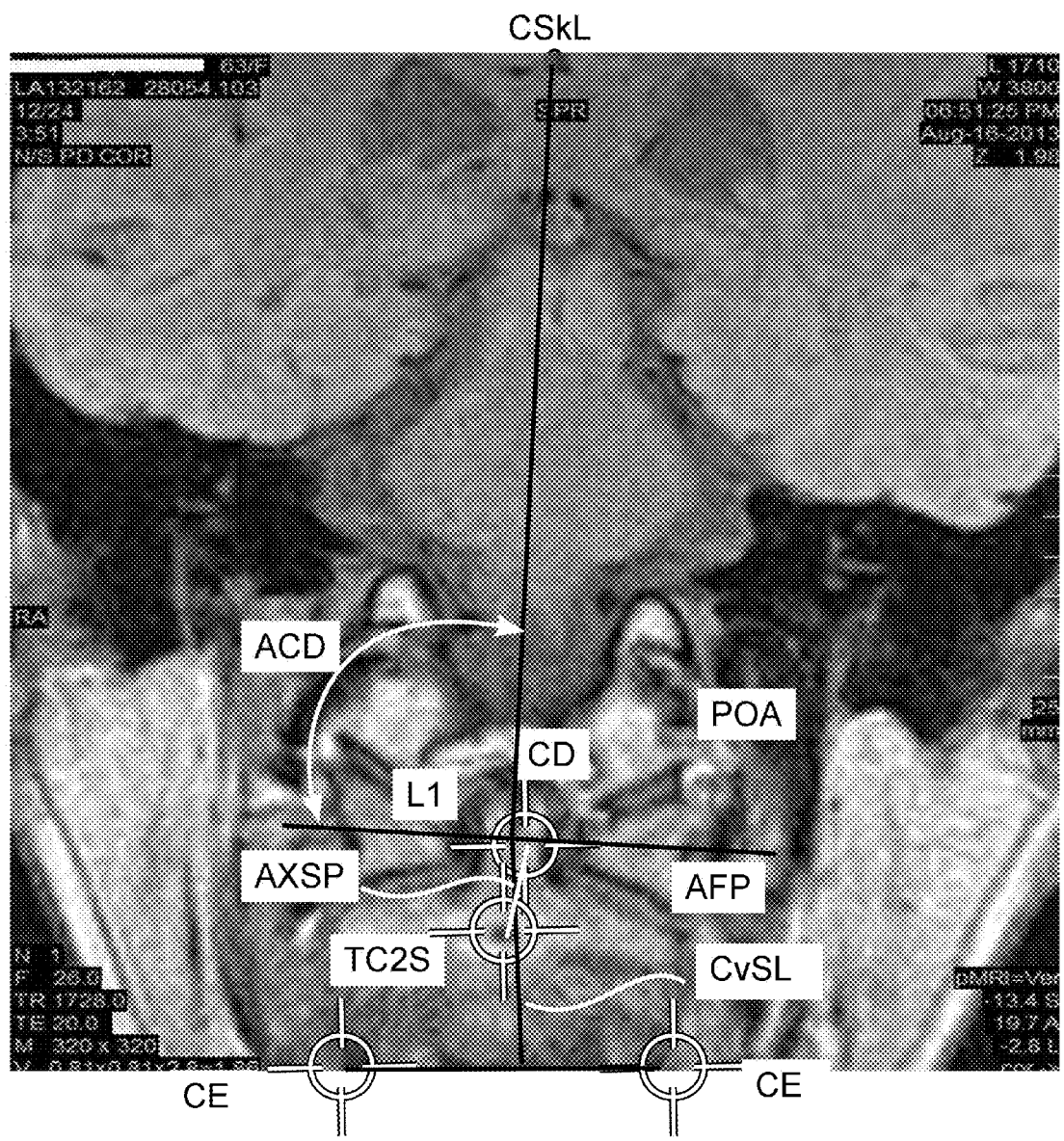
FIG. 8 is a different near coronal type MRI image with the same orientation and plane section as FIG. 4-6, showing anatomic markers and reference lines used to determine the side of the atlas that is used in FIG. 7 to determine the correction vector Y-axis component and perform the treatment illustrated in FIG. 2.

As shown in FIGS. 7 and 8, the other end of the CSpL is defined by a representative center point (RC) of the line L2 that extends generally horizontally between the edge (CE) of the vertebral body, C4 in this example, but optionally any C3-C7, but preferably the most representative fit thereof.

FIG. 7 also illustrates the disposition of the Reference Level Line (RLL) as orthogonal to the CSkL, as well as the Atlas Frontal Plane Line (AFP) that extends between the points of attachment (POA) of the opposing posterior arches of the right and left lateral masses of Atlas (C1). In FIG. 7, the A/C work factor is the angle between the RLL and the CvSL. The Circle tangent angle (CTA) work factor is the angle between the Lower Line (LL) and the Upper Line UL. Lower line (LL) extends along the axial surface of C2. Upper line (UL) runs along the occipital condyle of C1. The Atlas Frontal Plane (AFP) work factor is the distance in mm between the RLL and the APL at the jaw (AFPwf).

In addition, as illustrated in FIG. 8, deploying the same near coronal MRI images used to measure the work factors, the orientation of the Atlas Cephalic Displacement (ACD) from the CSkl is measured. Atlas Spinous Line (AXSP) distance in mm is measured from CD to TC2S. The ACD will then be used determine which lateral mass of C1 will be used to calculate the Y-axis component of the correction vector. The AXSP is used to position the head support platform 26 as shown in the FIG. 2B per the Atlas Orthogonal Chiropractic Basic I and/or II Manuals.

Figure 9:
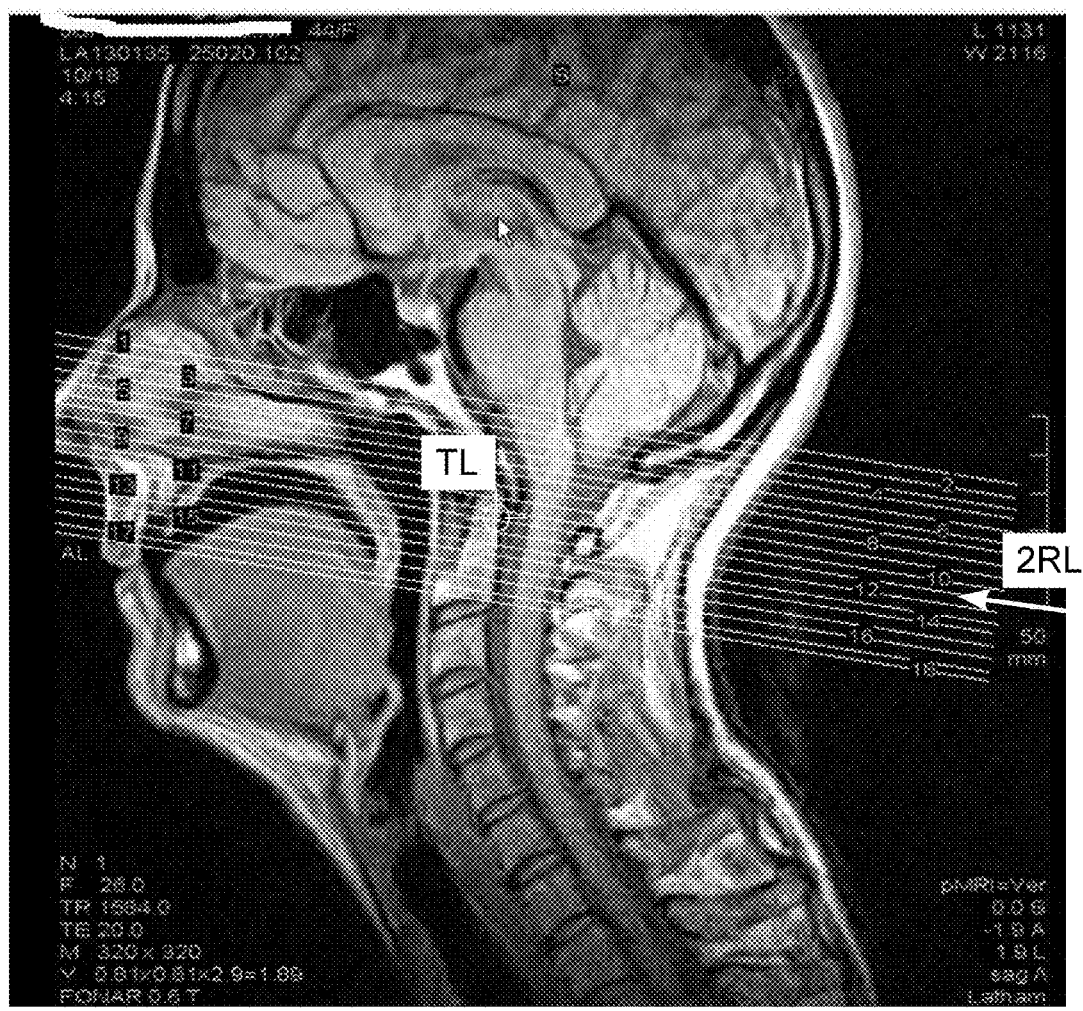
FIG. 9 is a sagittal MRI "scout" image (PD spin sequence) of the patient's skull and upper cervical region used to position a series of parallel axially oriented images planes for subsequent MRI acquisition, which are then used to identify anatomical reference points deployed in subsequent calculations of vector components of the stylus deployed in the treatment illustrated in FIGS. 2A and 2B

FIG. 9 is the "scout" sagittal MRI as used to position a series of parallel images planes for additional MRI images. One or more of these additional MRI images are used to identify anatomical reference points used to determine correction vector Y-component in the inventive method. This sagittal view was acquired with a PD spin sequence. In order to set the placement of the subsequent views, which are acquired at parallel spaced apart substantially orthogonal planes noted on the image a "stack" or sequence of parallel spaced apart planes is centered at the Transverse Ligament (TL), with the stack perpendicular to the back of the dens of C2, aids in capturing an image of the plane that passes through the lateral masses of the Atlas (C1).

Figure 10:
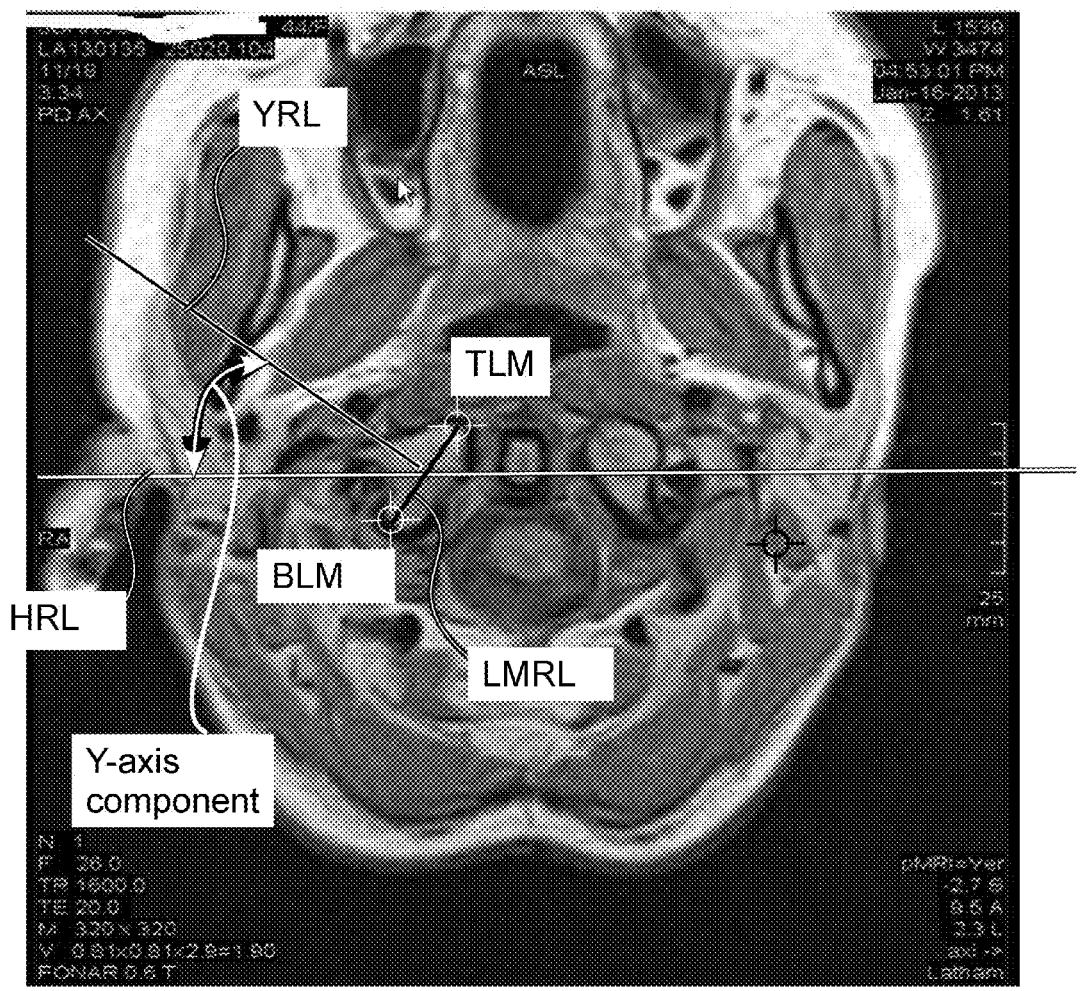
FIG. 10 is an axial MRI image of the plane slice no. 11 in the scout view of FIG. 9 used to identify anatomical reference points and determine the correction vector Y-axis component in the inventive method.
Figure 11:
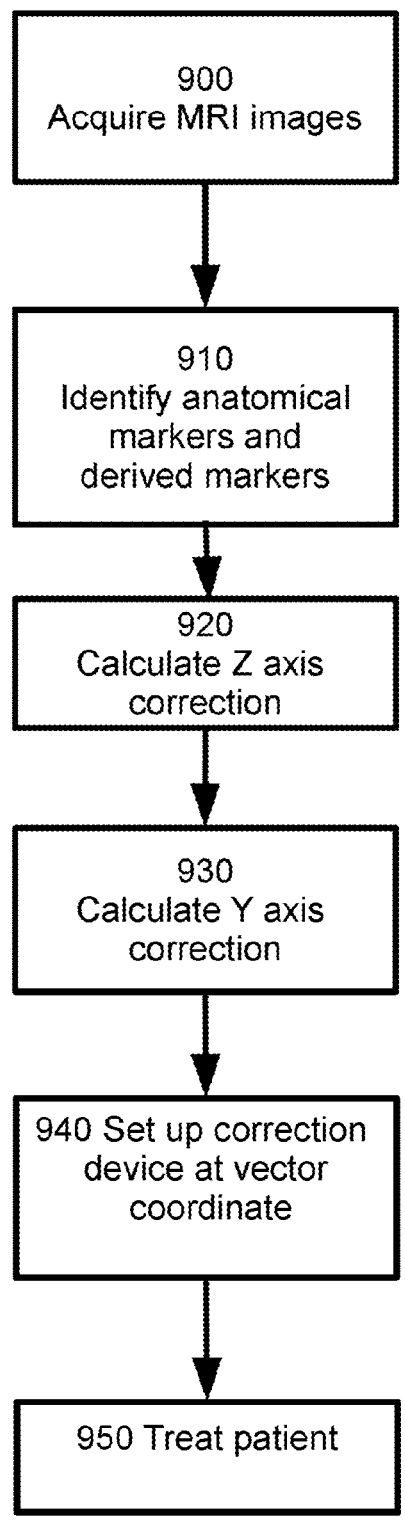
FIG. 11 is a process flow chart providing an overview of one aspect of the inventive imaging, analysis and treatment processes.

FIG. 10 is an axial MRI image (PD spin) at slice 2RL form FIG. 9, as used to identify anatomical reference points and determine correction vector Y axis components in the inventive method corresponding with steps 930-933. In calculating the Y-axis component of the correction vector, the target lateral mass of C1 is identified. The target lateral mass is the on the side of C1 that is raised upward in the patient, as determined from the measurement of the ACD as described with respect to FIG.

A Horizontal reference line (HRL) is drawn symmetrically from right to left sides of the skull to extends through one or both of the opposing lateral masses of C1. Next, after identifying the target lateral mass of the atlas C1 from the ACD orientation, a Lateral Mass Reference Line (LMRL) is drawn between the tip of the center of the bottom of lateral mass of C1 (BLM) to the to the center of the top lateral mass of C1 (TLM). Then another reference line (YRL) is drawn perpendicular to LMRL to longitudinal line of C1 lateral mass.

The Atlas Y correction vector components or rotation parameter is the angle between YRL and the HRL. When the lateral mass of C1 is shifted to the right, the stylus in FIG. 2B is from the right side of the patient, that is the patient lies with the upward shifted lateral mass of C1 disposed upward, so that the stylus 22 urges it downward into the correct position. Note this measurement is in sharp contrast to the prior art method and result using the superior facets of the lateral masses of the Atlas as shown in FIG. 1

Use of the proper MRI image enables the determination of an Atlas correction coordinate based on different anatomic features than the convention method and results in a more successful correction with respect to restoring CSF flow It has been discovered that the methods disclosed herein are superior in accounting for anatomic variations that frequently occur and would given rise to a different correction factor if derived using the standard method Atlas Orthogonal technique from a conventional x-ray radiograph.

However, owing to the scarcity and resource cost of upright MRI equipment, it is believed that correction calculation and method of the Y-component of the correction vector can be made from x-ray radiographs of clinically less challenging patients with satisfactory results.

Accordingly, in the interest of providing patient with cost effective follow up care, it is desirable to calculate the correction vector coordinates from both X-ray radiographs and MRI slices to determine the variance, so that future corrections of the patient can be made from future x-rays, by comparison to the initial x-ray so the practitioner can make a clinical judgment as to whether to apply the same variance to correct the subsequent x-ray (can we provide an example of this) variance, In clinical application of the above methods, patients were examined in an upright MRI utilizing cerebral spinal fluid (CSF) flow cine software, which allowed for evaluation of CSF flow. It was noted that in each patient there was a static misalignment of the 1st cervical vertebra (Atlas), as well as substantially reduced CSF flow at the cranio-cervical junction associated with cerebellar tonsillar ectopia. Both patients received a manipulation directed at the C1 misalignment utilizing the inventive correction procedure. Within an hour of the correction both patients were rescanned for CSF flow. In both cases restoration of normal flow was observed. Additionally, the headache pain level was nearly eliminated immediately post treatment in both patients. Subsequent follow-up has demonstrated persisting improvement in headache severity, with similar nearly instantaneous results with the same procedure of instrumented manipulation when the headaches symptoms have returned.

Prior research has demonstrated a correlation between CSF flow obstruction and intracranial pressure headaches. This is a potentially significant clinical finding (CSF obstruction) that can lead to long-term and often unexplained complaints of unresolved headaches, neck pain, paresthesias, numbness, and a variety of other symptoms that are often associated with cerebellar tonsillar ectopia. Further, the same methods of MRI imaging used to provide an analysis of abnormalities in CSF flow can include an assessment of the variation and maximum fluid pixel velocities at vertebral positions or portion of the cranio-erticular junction that show structural abnormalities, such as the relative displacement of vertebra, descended tonsils, impingement of the spinal canal by bulging or ruptured disks, as well as damage to other structural supporting soft tissues, such as tendons and ligaments.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

For examples, alternative types of stylus instruments, patient platforms and stylus support platforms can be used, as the inventor does not intend the scope of the claims to be limited to correction procedures performed solely with the Atlas Orthogonal instrument or methodology.

I claim:

1. A method of patient treatment comprising the steps of:
   a) obtaining at least one scout tomographic image of a skull and cervical spine of a patient,
   b) identifying at least one anatomical marker selected from an alar ligament and a transverse ligament in the scout tomographic image,
   c) acquiring at least a second tomographic image in a plane orthogonal to the at least one scout tomographic image, wherein the at least second tomographic image extends through the at least one anatomical marker identified in step b),
   d) identifying a position of each of a second plurality of anatomical markers in the at least second tomographic image,
   e) determining at least one vector component for orienting a stylus against at least a portion of an Atlas of the patient from the position of the second plurality of anatomical markers in the at least second tomographic image,
   f) energizing the stylus to provide a corrective impulse to the Atlas in a direction of the at least one vector component,
   g) acquiring at least a third tomographic image to confirm a corrective placement of the Atlas from said step of energizing the stylus.

2. The method of patient treatment according to claim 1, wherein the stylus approaches from above and forward of the patient, wherein the patient is positioned lying sideways, at the intersection of a mastoid bone and a ramus of a jaw of the patient to apply corrective force to a transverse process of the Atlas.

3. The method of patient treatment according to claim 1, wherein the vector component of the corrective impulse in a Y-axis coordinate is determined from an axial MRI tomographic image that includes at least one lateral mass of the Atlas and the Y-axis coordinate is the angle between:
   a horizontal reference line (HRL) that extends symmetrically from right to left sides of the skull, and
   a second reference line that is perpendicular to a third reference line,
   wherein the third reference line extends between a tip of a center of a bottom lateral mass of the Atlas, to a center of a top lateral mass of the Atlas.

4. The method of patient treatment according to claim 1, wherein the stylus is directed along a corrective vector having a Y- and Z-coordinate determined by MRI tomographic imaging means.

5. The method of patient treatment according to claim 4 wherein the MRI tomographic imaging means includes the steps of acquiring a first sagittal scout view of the skull and cervical region and at least one of an axial and near coronal view that is of a plane orthogonal to the sagittal scout view.

6. The method of patient treatment according to claim 4, wherein the patient is in an upright posture during the acquisition of the MRI tomographic images.

7. The method of patient treatment according to claim 1, wherein prior to said step of a) obtaining at least one scout tomographic image of the skull and cervical spine of the patient, the method further comprises the steps of:
   i) obtaining a first plurality of cine phase contrast MRI images to dynamically image a flow of at least one of cerebral spinal fluid (CSF) and blood, and
   ii) analyzing the cine phase contrast MRI to determine a potential correlation of misalignment or placement of at least one of C1-C7 with a coincident region of abnormal flow of at least one of cerebral spinal fluid (CSF) and blood.

8. The method of patient treatment according to claim 7 wherein after said step of g) acquiring a third tomographic image to confirm a corrective placement of the Atlas from said step of energizing the stylus, further comprising the steps of:
   obtaining a second plurality of cine phase contrast MRI images to dynamically image a flow of at least one of cerebral spinal fluid (CSF) and blood, and
   determining if the step of energizing the stylus to provide a corrective impulse to the Atlas has corrected the coincident regions of abnormal flow of at least one of cerebral spinal fluid (CSF) and blood.

\* \* \* \* \*